(12) United States Patent
Bernstein

(10) Patent No.: US 6,753,146 B1
(45) Date of Patent: Jun. 22, 2004

(54) SYSTEM AND METHOD FOR EVALUATING AGENTS WHICH PREVENT OXIDATIVE DAMAGE

(75) Inventor: Eric F. Bernstein, 1321 Grennox Rd., Wynnewood, PA (US) 19096

(73) Assignee: Eric F. Bernstein, Marlton, NJ (US)

( * ) Notice: Subject to any disclaimer, the term of this patent is extended or adjusted under 35 U.S.C. 154(b) by 0 days.

(21) Appl. No.: 09/913,472

(22) PCT Filed: Feb. 22, 2000

(86) PCT No.: PCT/US00/04438

§ 371 (c)(1),
(2), (4) Date: Jan. 28, 2002

(87) PCT Pub. No.: WO00/49876

PCT Pub. Date: Aug. 31, 2000

Related U.S. Application Data

(60) Provisional application No. 60/121,418, filed on Feb. 23, 1999.

(51) Int. Cl.[7] .............................. C12Q 1/68; C12N 5/10; C12N 15/09
(52) U.S. Cl. .............................. 435/6; 435/29; 435/325; 435/352; 435/357
(58) Field of Search .............................. 435/6, 29, 325, 435/352, 357; 800/13

(56) References Cited

U.S. PATENT DOCUMENTS

| | | | |
|---|---|---|---|
| 5,648,061 A | | 7/1997 | Bernstein et al. ............ 424/9.2 |
| 5,840,734 A | * | 11/1998 | Bernstein .................... 514/315 |
| 6,018,098 A | * | 1/2000 | Bernstein et al. ............ 800/18 |

FOREIGN PATENT DOCUMENTS

WO   WO 96/37237 A1 * 11/1996

OTHER PUBLICATIONS

Kawaguchi et al., "Effect of Reactive Oxygen Species on the Elastin mRNA Expression in Cultured Human Dermal Fibroblasts", *Free Radical Biology and Medicine* 1997 23(1):162–165.

Westermarck et al., "Suppression of Elastin Gene Expression in Dermal Fibroblasts by Protein Phosphatase Inhibitor Okadaic Acid", *Biochemical and Biophysical Research Communications* 1995 209(1):175–181.

* cited by examiner

Primary Examiner—Scott D. Priebe
(74) Attorney, Agent, or Firm—Licata & Tyrrell P.C

(57) ABSTRACT

An in vitro system for identifying agents capable of inhibiting or preventing oxidative damage is provided. The disclosed in vitro system comprises a mouse fibroblast culture derived from a transgenic mouse capable of expressing a reporter gene regulated by a human elastin promoter and a chemical means for generating reactive oxygen species within the mouse fibroblast culture. Also disclosed is a method for using this in vitro system for identifying agents capable of inhibiting or preventing oxidative damage. The disclosed method comprises adding a test agent suspected of providing protection against oxidative damage to the mouse fibroblast culture, adding a chemical means for generation of reactive oxygen species to the culture, determining human elastin promoter activity in the culture exposed to the test agent after a selected time period, and comparing the determined human elastin promoter activity in the culture exposed to the test agent to the activity of the same promoter in a control fibroblast culture wherein a decrease in the determined human elastin promoter activity is indicative of the test agent inhibiting or preventing oxidative damage.

2 Claims, No Drawings

SYSTEM AND METHOD FOR EVALUATING AGENTS WHICH PREVENT OXIDATIVE DAMAGE

RELATED APPLICATIONS

This application is a National Stage of PCT/US00/04438, filed Feb. 22, 2000, which claims priority to Provisional Application No. 60/121,418 filed Feb. 23, 1999.

BACKGROUND OF THE INVENTION

Chronic sun exposure eventuates in wrinkling, sagging, pigmentary alterations, and skin cancers which are characteristic of sun-damaged skin, and collectively referred to as photoaging (Kligman, A. M. JAMA 210:2377–2380, 1969; Gilchrest, B. A. J. Am. Acad. Dermatol. 21:610–613, 1989). The major histopathologic alteration in the dermis of photoaged skin underlying the wrinkling, sagging and yellow discoloration characterizing photoaged skin is the accumulation of large amounts of abnormal elastic material, termed solar elastosis replacing the normally collagen-rich dermis (Mera et al. Br. J. Dermatol. 117:21–27, 1987; Bernstein et al. J. Invest. Dermatol. 103:182–186, 1994). One of the primary events in the generation of solar elastosis is elastin promoter activation (Bernstein et al. J. Invest. Dermatol. 105, 269–273, 1995).

A transgenic mouse line expressing the human elastin promoter linked to a chloramphenicol acetyltransferase reporter gene (CAT) has been developed which models cutaneous photoaging in an in vivo and in vitro system (Bernstein et al. J. Invest. Dermatol. 105, 269–273, 1995). Although phenotypically normal, the cells in these mice possess the human elastin promoter/CAT construct, allowing elastin promoter activity to be measured in response to stimuli such as ultraviolet radiation (UV). These mice, and fibroblasts cultures derived from their skin, have been demonstrated to provide a rapid and sensitive means of identifying compounds capable of inhibiting cutaneous photodamage (Bernstein et al. J. Invest. Dermatol. 105, 269–273, 1995; Bernstein et al. Photochem. Photobiol. 64:369–74, 1996; Bernstein et al. J. Am. Acad. Dermatol. 37:725–729, 1997).

Among the various mechanisms by which UV damages skin is the generation of reactive oxygen species (Miyachi, Y. J. Dermatol. Sci. 9:79–86, 1995). Reactive oxygen species may form immediately as a result of UV exposure, or result from the inflammatory response which often follows UV-induced injury. Although the erythema of a sunburn is clinical evidence of damage from UV, an inflammatory infiltrate may be evident histopathologically even in the absence of erythema, and may result in continued exposure of the dermis to free radicals, days after the UV-induced damage has occurred (Kligman, A. M. JAMA 210:2377–2380, 1969; Lavker et al. J. Am. Acad. Dermatol. 32:53–62, 1995). The role of free radicals in cutaneous photodamage has been well documented (Ranadive, N. S. and Menon, I. A. Pathol. Immunopathol. Res. 5:118–139, 1986; Miyachi, Y and Imamura, S. Photodermatol. Photoimmunol. Photomed. 7:49–50 1990; Miyachi, Y. J. Dermatol. Sci. 9:79–86, 1995; and Peak et al. Photochem. Photobiol. 54:197–203, 1991). UV-induced free radical generation in skin has been demonstrated (Peak et al. Photochem. Photobiol. 54:197–203, 1991; and Norins, A. L. J. Invest. Dermatol. 39: 445–448, 1962). In addition, some enzymes which protect against oxidative damage, such as superoxide dismutase and catalase, are depleted after UV exposure (Pence, B. C. and Naylor, M. F. J. Invest. Dermatol. 95:213–216, 1990; Maeda et al. Photochem. Photobiol. 54:737–740, 1991; Shindo, Y and Hashimoto, T. J. Dermatol. Sci. 14:225–232, 1997), and antioxidants that scavenge free radicals have demonstrated protection against UV (DeRios et al. J. Invest. Dermatol. 70:123–125, 1975; and Bissett et al. J. Soc. Cosmet. Chem. 43:85–92, 1992). Investigators have recently demonstrated elastin mRNA production in response to free radicals generated using a xanthine and xanthine oxidase system in vitro, providing evidence for the role of oxidative stress in the generation of solar elastosis (Kawaguchi et al. Free Radical Biol. Med. 23:162–165, 1997).

It has now been demonstrated that reactive oxygen species stimulate elastin production at the promoter level in fibroblasts derived from a transgenic mouse model of cutaneous photoaging. Further, the ability of an agent known to protect against oxidative damage to inhibit stimulation of elastin production in this system has also been demonstrated. Accordingly, the present invention relates to an in vitro system and method for identifying agents capable of protecting against oxidative damage via a mouse fibroblast culture derived from a transgenic mouse capable of expressing human elastin promoter and a means for generating reactive oxygen species within the mouse fibroblast cultures.

SUMMARY OF THE INVENTION

An object of the present invention is to provide an in vitro system for identifying agents capable of inhibiting or preventing oxidative damage comprising a mouse fibroblast culture derived from a transgenic mouse capable of expressing human elastin promoter and a means for generating reactive oxygen species within the mouse fibroblast culture.

A method of identifying agents capable of inhibiting or preventing oxidative damage using this system is also provided.

DETAILED DESCRIPTION OF THE INVENTION

Oxidative damage may play a greater role in dermal, as compared to epidermal, damage from UV. Thus the generation of photoaging, clinically evident as wrinkling and sagging of skin, may result more from free radical-induced mechanisms than UV-induced skin cancers which originate in the epidermis. Evidence for this includes the greater sensitivity of fibroblasts to free radical-induced damage as compared to keratinocytes (Applegate, L. A. and Frenk, E. Photodermatol. Photoimmunol. Photomed. 11:95–101, 1995; Moysan et al. Photodermatol. Photoimmunol. Photomed. 11:192–197, 1995; Masaki, H. and Sakurai, H. J. Dermatol. Sci. 14:207–216, 1997), and the fact that circulating inflammatory cells which produce free radicals course through the dermis and less frequently invade the epidermis. Also the longer wavelengths of UV, which produce less direct DNA damage (Setlow, R. B. Science 153:379–386, 1966) but may exert their deleterious effects mainly through oxidative mechanisms, penetrate more deeply into skin, depositing much of their energy in the dermis. Thus, free radical mechanisms of damage may be the primary means by which UVA-induced photoaging takes place.

A number of effective sunscreens for blocking UVB are currently on the market, and increasing amounts of UVA protection are being incorporated into sunscreens to obtain higher sun protection factors. Further improvements are likely to result from incorporating effective free radical scavengers into currently available sunscreens. Accordingly, there is a need for a system of identifying agents which inhibit or prevent oxidative damage from the sun.

U.S. Pat. No. 5,648,061 discloses a transgenic mouse model which permits investigation of human elastin promoter activity in response to ultraviolet irradiation both in vivo by direct irradiation of mouse skin, and in vitro by irradiation of dermal fibroblasts grown from skin explants. It has now been demonstrated that generation of reactive oxygen species in these dermal fibroblasts via a hypoxanthine and xanthine-oxidase system results in a 6-fold increase in elastin promoter activity. Further, this increase can be eliminated by the addition of catalase, an enzyme known to protect against oxidative damage. Accordingly, incorporation of a means for generating reactive oxygen species such as a hypoxanthine and xanthine oxidase system within these mouse fibroblast cultures results in a sensitive system for evaluating agents which may prevent oxidative damage. Using this system agents which may protect against the oxidative damage resulting from UV exposure may be rapidly screened, and promising candidates identified for further study and eventual incorporation into sunscreens.

A series of experiments were performed with this new system.

In a first set of experiments, the optimum time span for incubation of fibroblasts, derived from the skin of transgenic mice, with a hypoxanthine and xanthine oxidase system was determined by exposing cells to a hypoxanthine and xanthine oxidase system for increasing amounts of time, and determining CAT activity as outlined in Example 3 after a 24 hour incubation. CAT activity increased steadily until a peak occurred after 90 minutes of incubation. Longer incubation times resulted in excessive cell toxicity and a corresponding decrease in CAT activity. Thus, a 90 minute incubation time for cells to be in contact with hypoxanthine and xanthine oxidase was selected for further studies.

The addition of hypoxanthine and xanthine oxidase to fibroblast cultures for 90 minutes increased human elastin promoter activity as determined by CAT assay to 6.0±0.6-fold (mean±sem) that of untreated control cells. The addition of 10,000 U/ml of catalase just prior to hypoxanthine and xanthine oxidase exposure fully eliminated this increase. Catalase-treated cells exposed to hypoxanthine and xanthine oxidase demonstrated no increase over control cells, with a mean of 1.0±0.1-fold of untreated controls. Trypan blue exclusion demonstrated less than 15% toxicity in cells treated with hypoxanthine/xanthine oxidase and hypoxanthine/xanthine oxidase plus catalase.

Accordingly, these mouse fibroblast cultures which express the human elastin promoter and comprise a means for generation of reactive oxygen species such as a hypoxanthine and xanthine oxidase system provide a useful system for identifying agents capable of protecting against oxidative damage. Test agents suspected of providing protection against oxidative damage can be added to the mouse fibroblast culture prior to addition of the means for generation of reactive oxygen species. The means for generating reactive oxygen species is then added and human elastin promoter activity is determined in the mouse fibroblast culture after a selected time period, preferably 90 minutes for a hypoxanthine and xanthine oxidase system. In a preferred embodiment, elastin promoter activity is determined by measuring expression of the reporter gene, i.e. the CAT activity, of the mouse fibroblast culture. Human elastin promoter activity in the mouse fibroblast culture exposed to the test agent is then compared to elastin promoter activity in a control fibroblast culture not exposed to the test agent but still exposed to the means for generating reactive oxygen species. Agents providing protection against oxidative damage are identified as those test agents which decrease human elastin promoter activity in the mouse fibroblast culture exposed to the test agent and the means for generating reactive oxygen species as compared to the control fibroblast culture.

The following nonlimiting examples are provided to further illustrate the present invention.

EXAMPLES

Example 1

Fibroblast Cultures Expressing the Human Elastin Promoter

Fibroblasts derived from the skin of a homozygous line of transgenic mice expressing the 5.2-kb human elastin promoter, linked to a CAT reporter gene which enables measurement of elastin promoter activation, as previously described (Bernstein et al. J Invest Dermatol 105, 269–273, 1995; and Bernstein et al. Photochem Photobiol 64:369–74, 1996) were utilized. Although phenotypically normal, these mice express the human elastin promoter when assayed for CAT activity (Hsu-Wong et al. J. Biol. Chem. 269: 18072–18075, 1994; Bernstein et al. J Invest Dermatol 105, 269–273, 1995; and Bernstein et al. Photochem Photobiol 64:369–74, 1996).

Fibroblast cultures were established from the skin of transgenic mice by explanting tissue specimens onto plastic tissue-culture dishes and allowing cells to migrate to the area of the dish surrounding the explants. The primary cultures were maintained in Dulbecco's modified Eagle's medium (DMEM) supplemented with 10% fetal calf serum (FCS), 2 mM L-glutamine and antibiotics, at 37° C. The primary cell cultures were passaged by trypsinization, and the subcultures in passages three or four were exposed to hypoxanthine/xanthine oxidase.

Example 2

Exposure to Free Radicals Generated by Hypoxanthine/Xanthine Oxidase

DMEM with 10% FCS was removed, cells were rinsed in phosphate buffered saline (PBS), and DMEM was replaced without the addition of FCS. Both 500 $\mu$M hypoxanthine (Sigma Chemical Co., St. Louis, Mo.) and 80 mU/ml xanthine oxidase (Sigma Chemical Co., St. Louis, Mo.) were then added to fibroblast cultures which were incubated for 90 minutes at 37° C. The concentrations of hypoxanthine and xanthine oxidase were selected based on previous work by Mitchell et al. (Biochemistry 29:2802–2807, 1990). The optimum time span for incubation of cells with hypoxanthine/xanthine oxidase was determined by exposing cells to hypoxanthine/xanthine oxidase for 15, 30, 60, 90 and 120 minutes and determining CAT activity as outlined in Example 3. After exposure to hypoxanthine/xanthine oxidase, cells were rinsed in PBS and incubated in DMEM with FCS for 24 hours, which is the time maximal promoter activation was determined to occur after exposure to hypoxanthine/xanthine oxidase and then harvested for determination of CAT activity (Hsu-Wong et al. J. Biol. Chem. 269: 18072–18075, 1994; Bernstein et al. J Invest Dermatol 105, 269–273, 1995; and Bernstein et al. Photochem Photobiol 64:369–74, 1996). Control cells were treated in an identical fashion without the addition of hypoxanthine/xanthine oxidase.

In addition to hypoxanthine/xanthine oxidase treatment alone, cells were also treated with hypoxanthine/xanthine oxidase plus 10,000 U/ml of catalase (Sigma Chemical Co., St. Louis, Mo.) co-incubated for 90 minutes, and harvested as outlined above 24 hours following treatment. Fibroblasts from mice representing the same litter were used for any given experiment. Four dishes of cells were used for each experimental condition (control, hypoxanthine/xanthine oxidase, and hypoxanthine/xanthine oxidase+catalase), and experiments were repeated in duplicate, yielding a total of eight values for each experimental condition.

The effect of hypoxanthine/xanthine oxidase and hypoxanthine/xanthine oxidase+catalase on cell viability was determined using the trypan blue (Sigma Chemical Co., St. Louis, Mo.) exclusion method (Ausubel et al. Short protocols in molecular biology. John Wiley & Sons, Inc., 2nd ed., New York, 1992 p.11–24), and a paired t-test analysis was performed for statistical evaluation of the data.

Example 3

CAT Assay

To measure the expression of the human elastin promoter/CAT reporter gene construct in the skin of transgenic mice and in fibroblast cultures established from these animals, CAT activity was determined. For extraction of the CAT from skin, the specimens were homogenized in 0.25 Tris-HCl, pH 7.5, using a tissue homogenizer (Brinkmann Instruments, Inc. Westbury, N.Y.). The homogenates were centrifuged at 10,000×g for 15 minutes at 4° C. and the protein concentration in the supernatant determined by a commercial protein assay kit (Bio-Rad Laboratories, Richmond, Calif.). Aliquots of the supernatant containing 100 μg of protein were used for assay of CAT activity by incubation with [$^{14}$C] chloramphenicol in accordance with well-known procedures. The acetylated and non-acetylated forms of radioactive chloramphenicol were separated by thin-layer chromatography and CAT activity was determined by the radioactivity in the acetylated forms as a percent of the total radioactivity in each sample.

What is claimed is:

1. An in vitro system for identifying agents capable of inhibiting or preventing oxidative damage comprising:
   a cell culture which expresses a reporter gene regulated by a human elastin promoter; and
   a chemical means for generating reactive oxygen species within the cell culture, said chemical means for generating reactive oxygen species being a hypoxanthine and xanthine oxidase system.

2. A method for identifying agents capable of inhibiting or preventing oxidative damage comprising:
   adding a test agent suspected of providing protection against oxidative damage to a cell culture which expresses a reporter gene regulated by a human elastin promoter;
   adding a chemical means to the cell culture for generating reactive oxygen species in the cell culture, said chemical means for generation of reactive oxygen species being a hypoxanthine and xanthine oxidase system;
   determining human elastin promoter activity in the cell culture exposed to the test agent after a selected period of time; and
   comparing the determined human elastin promoter activity in the cell culture exposed to the test agent to human elastin promoter activity in a control cell culture, wherein a decrease in the determined human elastin promoter activity is indicative of the test agent inhibiting or preventing oxidative damage.

* * * * *